United States Patent
Lin et al.

(10) Patent No.: US 11,202,812 B2
(45) Date of Patent: Dec. 21, 2021

(54) REDUCING BODY FAT PROBIOTIC STRAIN, COMPOSITION THEREOF, AND USE THEREOF

(71) Applicant: TCI CO., LTD., Taipei (TW)

(72) Inventors: Yung-Hsiang Lin, Taipei (TW); Chu-Han Huang, Taipei (TW); Cheng-Yu Ho, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 16/731,305

(22) Filed: Dec. 31, 2019

(65) Prior Publication Data

US 2020/0306324 A1 Oct. 1, 2020

Related U.S. Application Data

(60) Provisional application No. 62/825,803, filed on Mar. 29, 2019.

(51) Int. Cl.
*A61K 35/747* (2015.01)
*A23L 33/135* (2016.01)
*A61P 3/04* (2006.01)

(52) U.S. Cl.
CPC .......... *A61K 35/747* (2013.01); *A23L 33/135* (2016.08)

(58) Field of Classification Search
CPC ....... A61K 35/747; A23L 33/135; A23L 2/52; A23V 2002/00; A23V 2200/332; A61P 3/04
See application file for complete search history.

(56) References Cited

U.S. PATENT DOCUMENTS

2011/0268702 A1* 11/2011 Fukushima .......... A61K 31/733
424/93.3

FOREIGN PATENT DOCUMENTS

| CN | 101341254 A | 1/2009 |
|---|---|---|
| CN | 102026554 A | 4/2011 |

OTHER PUBLICATIONS

Bisig et al. Influence of processing on the fatty acid composition and the content of conjugated linoleic acid in organic and conventional dairy products—a review. Lait. 2007;87:1-19.*
Kim et al. Impact of Conjugated Linoleic Acid (CLA) on Skeletal Muscle Metabolism. Lipids. 2016;51:159-178.*
Examination report dated Sep. 15, 2020, listed in correspondent Taiwan patent application No. 108148719 (publication No. TW202034934).
Examination report dated Jan. 28, 2021, listed in correspondent Taiwan patent application No. 108148719 (publication No. TW202034934).
A rapid method of screening lactic acid bacterial strains for conjugated linoleic acid production., Romero-Perez GA et al., Bioscience, Biotechnology, and Biochemistry, Mar. 7, 2013, 77(3): p. 648-650.
Examination report dated Sep. 10, 2021, listed in correspondent China patent application No. 201911405436.8 (publication No. CN 111743921 A).
A Rapid Method of Screening Lactic Acid Bacterial Strains for Conjugated Linoleic Acid Production , Gustavo A. et al., Biosci. Biotechnol. Biochem., 77(3), 648-650, 2013, Abstract.

* cited by examiner

*Primary Examiner* — Lynn Y Fan
(74) *Attorney, Agent, or Firm* — Chieh-Mei Wang

(57) ABSTRACT

The present invention provides a method of reducing body fat, comprising administering a composition comprising an effective amount of *Lactobacillus paracasei* or a metabolite thereof to a subject in need thereof. The *Lactobacillus paracasei* or the metabolite thereof can effectively convert the fatty acid into conjugated linoleic acid, inhibit the accumulation of fat and promote the decomposition of fat in fat cells, and can effectively reduce the percentage of body fat, waist circumference, and hip circumference, and simultaneously increase the muscle mass of the subject.

8 Claims, 5 Drawing Sheets

REDUCING BODY FAT PROBIOTIC STRAIN, COMPOSITION THEREOF, AND USE THEREOF

CROSS-REFERENCE TO RELATED APPLICATION

This application claims priority of U.S. provisional application No. 62/825,803, filed on Mar. 29, 2019 the content of which is incorporated herein in its entirely by reference.

BACKGROUND OF THE INVENTION

1. Field of the Invention

The present invention relates to a reducing body fat probiotic strain, composition thereof and use thereof, and more particularly to the *Lactobacillus paracasei* subsp *paracasei* and the metabolite thereof for converting fatty acids into conjugated linoleic acid, inhibiting the accumulation of fat, promoting the decomposition of fat, and promoting the body weight loss and preventing re-fat of subjects.

2. The Prior Art

The World Health Organization (WHO) described "rapid disease" as a rapidly spreading obesity and called it "Globesity." With the changes in eating habits and the improvement of quality of life, the prevalence of obesity in Taiwan has also increased year by year. According to the survey on the changes in national nutrition and health status announced by the National Health Promotion Administration, Ministry of Health and Welfare, Taiwan, the prevalence rate of overweight or obesity in adults is as high as 43%; wherein, the ratio of male and female is 49% and 40% respectively. That is, every two men in Taiwan get one overweight or obese and every two to three women get one overweight or obese, and more than 200,000 of them have reached the standard of morbid obesity which must be treated with surgery.

Obesity could cause many related comorbidities, such as diabetes, hyperlipidemia, sleep apnea, angina, degenerative arthritis, high uric acid, and even some cancers, which may cause death, so the average life expectancy of patients with morbid obesity is much less than that of normal person. At present, the most effective method for treating obesity is surgery. In addition, legal drugs (currently only Xenical®), exercise, calorie control, and low-calorie meals have also proven to be effective methods. However, in addition to surgical treatment, most patients using other methods to lose weight are easy to lose their wariness and regain weight after the weight loss treatment is over, and the phenomenon of becoming thinner and then getting fat again is more harmful to the body.

In summary, in response to the changes in obesity and overall health problems caused by obesity while changes in living styles and eating habits, and based on the improvement of living standards and the improvement of the concept of health care, it is necessary to develop a composition which can effectively reduce body fat and the chances of regaining weight.

SUMMARY OF THE INVENTION

To solve the foregoing problem, one objective of the present invention is to provide a method of reducing body fat, comprising administering a composition comprising an effective amount of *Lactobacillus paracasei* subsp *paracasei* or a metabolite thereof to a subject in need thereof, and the *Lactobacillus paracasei* subsp *paracasei* is *Lactobacillus paracasei* subsp *paracasei* DSMZ33286, and the effective amount of the *Lactobacillus paracasei* subsp *paracasei* is $5\times10^9$ CFUs per day.

In one embodiment of the present invention, the *Lactobacillus paracasei* subsp *paracasei* or the metabolite thereof converts a fatty acid to a conjugated linoleic acid, and the effective amount of the *Lactobacillus paracasei* subsp *paracasei* is $1\times10^6$ CFUs per day.

In one embodiment of the present invention, the *Lactobacillus paracasei* subsp *paracasei* or the metabolite thereof inhibits the accumulation of fat in a fat cell or promotes the breakdown of fat in a fat cell.

In one embodiment of the present invention, the *Lactobacillus paracasei* subsp *paracasei* or the metabolite thereof reduces the percentage of whole body fat, the percentage of trunk body fat, the waist circumference, or the hip circumference of the subject.

In one embodiment of the present invention, the *Lactobacillus paracasei* subsp *paracasei* or the metabolite thereof increases the whole body muscle, or the trunk muscle mass.

The active strain of the *Lactobacillus paracasei* subsp *paracasei* TCI058 or the metabolite thereof can effectively convert the fatty acid in food into conjugated linoleic acid in vitro, which indicates that the *Lactobacillus paracasei* subsp *paracasei* TCI058 or the metabolite thereof has the potential to reduce the accumulation and retention of body fat in a subject and to promote the conversion of stored fat in a subject into energy. In the cell experiment, the *Lactobacillus paracasei* subsp *paracasei* TCI058 of the present invention or the metabolite thereof was found can effectively inhibit the accumulation of fat in fat cells and at the same time effectively promote the decomposition of fat in fat cells to reduce the content of fat in fat cells. In body experiments, the *Lactobacillus paracasei* subsp *paracasei* TCI058 of the present invention or the metabolite thereof was found can effectively reduce the percentage of whole body fat, the percentage of trunk body fat, the waist circumference, and the hip circumference of the subject, and can simultaneously increase the whole body muscle, or the trunk muscle mass to effectively reduce the fat content in subjects, and promote the body weight loss and prevent re-fat of subjects. Therefore, the *Lactobacillus paracasei* subsp *paracasei* TCI058 of the present invention or the metabolite thereof can be used for the preparation of a composition for reducing body fat, which is a food, a drink, a nutritional supplement, or a pharmaceutical product, and the composition is in a form of a powder, a granule, a solution, a gel can be administered to a subject in need by oral administration or the like.

The embodiments of the present invention are further described with the following drawings. The following embodiments are given to illustrate the present invention and are not intended to limit the scope of the present invention, and those having ordinary skill in the art can make some modifications and refinements without departing from the spirit and scope of the present invention. Therefore, the scope of the present invention is defined by the scope of the appended claims.

DETAILED DESCRIPTION OF THE PREFERRED EMBODIMENT

The *Lactobacillus paracasei* of the present invention is a probiotic bacteria that can convert the fatty acid in food into conjugated linoleic acid to reduce the content of body fat in a subject. The novel *Lactobacillus paracasei* strain of the present invention was obtained by screening on pineapple skin, and was named as TCI058 in the specification. The *Lactobacillus paracasei* TCI058 was registered in the Food Industry Research and Development Institute (Taiwan) on Apr. 15, 2019, and the number is BCRC910882. The *Lactobacillus paracasei* TCI058 was also deposited at the Leibniz Institute DSMZ (Address: Inhoffenstr. 7 B D-38124 Braunschweig). Germany, in accordance with the Budapest Treaty, on Sep. 19, 2019, under the registration number DSMZ 33286. Viability test of the bacterial strain was performed and confirmed on Oct. 7, 2019. The *Lactobacillus paracasei* TCI058 was cultured at 37° C. with MRS medium (de Man, Rogosa and Sharpe, BD Difco™ Lactobacilli MRS Broth). *Lactobacillus paracasei* is a Gram-positive bacterium and is a facultative hetero-fermentative lactic acid bacterium, which is commonly used in the fermentation of dairy products. The cells of *Lactobacillus paracasei* are rod-shaped, with a width of 2.0-4.0 μm and a length of 0.8-1.0 μm; *Lactobacillus paracasei* genotype and phenotype are similar to other strains of its genus, such as *Lactobacillus casei* and *Lactobacillus rhamnosus*; the genome of *Lactobacillus paracasei* contains a circular DNA and is slightly different between the different strains isolated. On average, the genomes of different strains have 29-30 thousand base pairs, and the GC content is 46.2-46.6%, and is expected to encode about 2800-3100 proteins; the known *Lactobacillus paracasei* has the effect of regulating the immune capacity of individuals, including inhibiting allergic reaction-related diseases, reducing respiratory inflammation, improving atopic dermatitis, etc.

Figure 1:
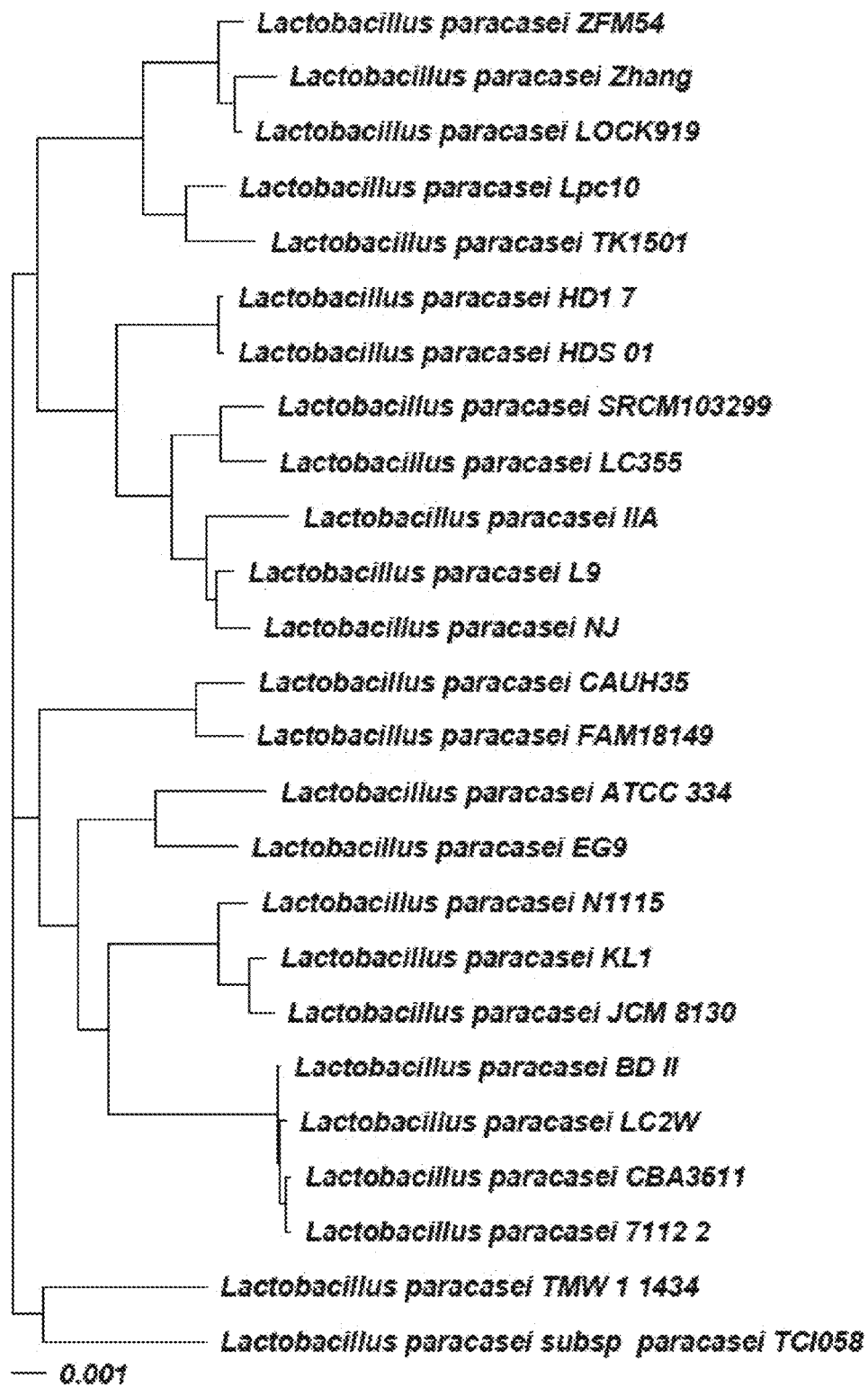
FIG. 1 shows the phylogenomic analysis of the *Lactobacillus paracasei* subsp *paracasei* TCI058 of the present invention and other *Lactobacillus paracasei* strains.

The novel *Lactobacillus paracasei* subsp *paracasei* TCI 058 strain of the present invention has the effect of reducing body fat of individuals. The genotype comparison with many different *Lactobacillus paracasei* subsp *paracasei* strains was shown in Table 1. As shown in Table 1, the total length of the genome of the *Lactobacillus paracasei* subsp *paracasei* TC 058 strain of the present invention is 30,500 base pairs, with 1 contig, encoding 3089 proteins (CDS, Coding sequence), and 212 of which are unique encoding proteins of the *Lactobacillus paracasei* subsp *paracasei* TCI 058 strain of the present invention. The phylogenomic analysis of the *Lactobacillus paracasei* subsp *paracasei* TCI058 strain of the present invention and other *Lactobacillus paracasei* subsp *paracasei* strains was shown in FIG. 1. As shown in FIG. 1, most of the other *Lactobacillus paracasei* subsp *paracasei* strains belong to different classifications with the *Lactobacillus paracasei* subsp *paracasei* TCI 058 strain of the present invention, and are only close to those of *Lactobacillus paracasei* subsp *paracasei* TMW 1_1434. The present invention was confirmed by an in vitro experiment that the *Lactobacillus paracasei* subsp *paracasei* TC058 or the metabolite thereof can effectively convert the fatty acid in food into conjugated linoleic acid, which indicates that the *Lactobacillus paracasei* subsp *paracasei* TCI058 or the metabolite thereof has the potential to reduce the accumulation and retention of body fat in a subject and to promote the conversion of stored fat in a subject into energy. It was confirmed by the cell experiment that the *Lactobacillus paracasei* subsp *paracasei* TCI058 of the present invention or the metabolite thereof could effectively inhibit the accumulation of fat in fat cells and at the same time effectively promote the decomposition of fat in fat cells to reduce the content of fat in fat cells. It was confirmed by the body experiment that the *Lactobacillus paracasei* subsp *paracasei* TCI058 of the present invention or the metabolite thereof could effectively reduce the percentage of whole body fat, the percentage of trunk body fat, the waist circumference, and the hip circumference of the subject, and can simultaneously increase the whole body muscle, or the trunk muscle mass to effectively reduce the fat content in subjects, and promote the body weight loss and prevent re-fat of subjects. Therefore, the *Lactobacillus paracasei* subsp *paracasei* TCI058 of the present invention or the metabolite thereof can be used for the preparation of a composition for reducing body fat, which is a food, a drink, a nutritional supplement, or a pharmaceutical product, and can be administered to a subject in need by oral administration or the like.

TABLE 1

The genotype comparison of different *Lactobacillus paracasei* strains

| Species | Genome Length (Mbp) | Contigs | CDS | Unique CDS |
|---|---|---|---|---|
| *Lactobacillus paracasei* TCI058 | 3.05 | 1 | 3089 | 212 |
| *Lactobacillus paracasei* LC355 | 3.14 | 3 | 3166 | 112 |
| *Lactobacillus paracasei* ZFM54 | 3.05 | 3 | 3100 | 93 |

TABLE 1-continued

The genotype comparison of different *Lactobacillus paracasei* strains

| Species | Genome Length (Mbp) | Contigs | CDS | Unique CDS |
|---|---|---|---|---|
| *Lactobacillus paracasei* CAUH35 | 2.97 | 5 | 3073 | 205 |
| *Lactobacillus paracasei* BD_II | 3.13 | 2 | 3225 | 38 |
| *Lactobacillus paracasei* LOCK919 | 3.14 | 2 | 3205 | 132 |
| *Lactobacillus paracasei* KL1 | 2.92 | 1 | 3018 | 145 |
| *Lactobacillus paracasei* Zhang | 2.9 | 2 | 2884 | 63 |
| *Lactobacillus paracasei* LC2W | 3.08 | 2 | 3156 | 27 |
| *Lactobacillus paracasei* TK1501 | 2.94 | 1 | 2936 | 58 |
| *Lactobacillus paracasei* L9 | 3.08 | 1 | 3092 | 73 |
| *Lactobacillus paracasei* HD1_7 | 3.04 | 1 | 3096 | 24 |
| *Lactobacillus paracasei* CBA3611 | 3.1 | 2 | 3184 | 46 |
| *Lactobacillus paracasei* TMW 1_1434 | 3.17 | 2 | 3148 | 156 |
| *Lactobacillus paracasei* Lpc10 | 3.05 | 1 | 3107 | 155 |
| *Lactobacillus paracasei* NJ | 3.08 | 1 | 3088 | 85 |
| *Lactobacillus paracasei* EG9 | 3.07 | 4 | 3210 | 253 |
| *Lactobacillus paracasei* N1115 | 3.06 | 5 | 3177 | 199 |
| *Lactobacillus paracasei* SRCM103299 | 3.19 | 3 | 3242 | 138 |
| *Lactobacillus paracasei* 7112_2 | 3.1 | 2 | 3174 | 41 |
| *Lactobacillus paracasei* HDS_01 | 3.04 | 1 | 3096 | 23 |
| *Lactobacillus paracasei* IIA | 3.25 | 4 | 3292 | 186 |
| *Lactobacillus paracasei* JCM 8130 | 3.02 | 3 | 3118 | 163 |
| *Lactobacillus paracasei* ATCC 334 | 2.92 | 2 | 2764 | 98 |
| *Lactobacillus paracasei* FAM18149 | 2.97 | 6 | 3109 | 252 |

Statistical analysis is performed using Excel software. Data are expressed as mean±standard deviation (SD), and the differences between these are analyzed by Student's t-test.

Definition

The data provided in the present invention represent approximated, experimental values that may vary within a range of ±20%, preferably ±10%, and most preferably ±5%.

The "probiotic" or "probiotic bacteria" describes herein is a microorganism, the cells thereof, the mixed strains, the extracts thereof or the metabolites thereof with a positive effect on the host itself, usually derived from the human body and beneficial to intestinal health. Probiotic or probiotic bacteria can also refer to certain microorganisms that are externally supplemented and are beneficial to the body. The metabolite thereof is a substance which is secreted into the bacterial culture solution after being metabolized by the bacteria, comprising the culture medium for culturing the bacteria, etc.

According to the present invention, the operating procedures and parameter conditions for bacterial culture are within the professional literacy and routine techniques of those having ordinary skill in the art.

The "effective concentration" or "effective amount" describes herein is that the required amount of the *Lactobacillus paracasei* subsp *paracasei* TCI058 of the present invention or the metabolite thereof for effectively converting fatty acids into conjugated linoleic acid, effectively inhibiting the accumulation of fat in fat cells, effectively promoting the decomposition of fat in fat cells, effectively reducing the percentage of whole body fat, the percentage of trunk body fat, the waist circumference, and the hip circumference of the subject, or effectively increasing increase the whole body muscle, or the trunk muscle mass of the subject. The effective concentration or effective amount would vary depending on the subject to which it is administered, but the effective concentration can be determined experimentally by, for example, a dose escalation test.

According to the present invention, a pharmaceutical product can be manufactured into a form suitable for parenterally or topically administration using techniques well known to those having ordinary skill in the art, including, but not limited to, injection (for example, sterile aqueous solution or dispersion), sterile powder, external preparation, and the like.

According to the present invention, the pharmaceutical product could further comprise a pharmaceutically acceptable carrier that is widely used in pharmaceutical manufacturing techniques. For example, the pharmaceutically acceptable carrier can comprise one or more agents selected from the group consisting of a solvent, a buffer, an emulsifier, a suspending agent, a decomposer, a disintegrating agent, a dispersing agent, a binding agent, an excipient, a stabilizing agent, a chelating agent, a diluent, a gelling agent, a preservative, a wetting agent, a lubricant, an absorption delaying agent, a liposome, and the like. The selection and quantity of these reagents falls within the professional literacy and routine skills of those having ordinary skill in the art.

According to the present invention, the pharmaceutically acceptable carrier comprises a solvent selected from the group consisting of water, normal saline, phosphate buffered saline (PBS), aqueous solution containing alcohol, and combinations thereof.

According to the present invention, the pharmaceutical product can be administered by a parenteral route selected from the group consisting of subcutaneous injection, intraepidermal injection, intradermal injection and intralesional injection.

According to the present invention, the pharmaceutical product can be manufactured into an external preparation suitable for topical application to the skin using techniques well known to those having ordinary skill in the art, including, but not limited to, an emulsions, a gel, an ointment, a cream, a patch, a liniment, a powder, an aerosol, a spray, a lotion, a serum, a paste, a foam, a drop, a suspension, a salve, and a bandage.

According to the present invention, the external preparation is prepared by mixing the pharmaceutical product of the present invention with a base which is well known to those having ordinary skill in the art.

According to the invention, the substrate could comprise one or more additives selected from the group consisting of water, an alcohol, a glycol, a hydrocarbon [such as petroleum jelly, and white petrolatum], a wax [such as paraffin and yellow wax], a preserving agent, an antioxidant, a surfactant, an absorption enhancers, a stabilizing agent, a gelling agent [such as Carbopol®974P, microcrystalline cellulose, and carboxymethylcellulose], an active agent, a humectant, an odor absorber, a fragrance, a pH adjusting agent, a chelating agent, an emulsifier, an occlusive agent, an emollient, a thickener, a solubilizing agent, a penetration enhancer, an anti-irritant, a colorant, a propellant, and the like. The selection and quantity of these additives falls within the professionalism and routine technology of those having ordinary skill in the art.

According to the present invention, the food product can be used as a food additive, added by the conventional method in the preparation of the raw material, or added during the production of the food, and matched with any edible material to be made into food products for human and non-human animals.

According to the present invention, the types of the food products include, but are not limited to, beverages, fermented foods, bakery products, health foods, and dietary supplements.

The present invention provides a method of reducing body fat, comprising administering to a subject in need thereof a composition composted of an effective amount of the *Lactobacillus paracasei* subsp *paracasei* TCI058 or the metabolite thereof, wherein the metabolites of the *Lactobacillus paracasei* subsp *paracasei* TCI058 of the present invention is obtained by taking the culture solution of the *Lactobacillus paracasei* subsp *paracasei* TCI058. The *Lactobacillus paracasei* subsp *paracasei* TCI058 of the present invention or the metabolite thereof can convert the fatty acid in food into conjugated linoleic acid, effectively inhibit the accumulation of fat in fat cells and at the same time effectively promote the decomposition of fat in fat cells, and effectively reduce the percentage of whole body fat, the percentage of trunk body fat, the waist circumference, and the hip circumference of the subject, and can simultaneously increase the whole body muscle, or the trunk muscle mass to effectively reduce the fat content in subjects.

Meanwhile, the composition for reducing body fat of the present invention could further comprise an effective amount of the *Lactobacillus paracasei* subsp *paracasei* TCI058 of the present invention or the metabolite thereof, and a pharmaceutically acceptable carrier, and the composition is a food, a drink, a nutritional supplement, or a pharmaceutical product.

The tests of the *Lactobacillus paracasei* subsp *paracasei* TCI058 of the present invention or the metabolite thereof for converting the fatty acid in food into conjugated linoleic acid in vitro, for inhibiting the accumulation of fat in fat cells, for promoting the decomposition of fat in fat cells, for reducing the percentage of whole body fat, the percentage of trunk body fat, the waist circumference, and the hip circumference of the subject, and simultaneously increasing the whole body muscle, or the trunk muscle mass will all be described in detail below to confirm that the *Lactobacillus paracasei* subsp *paracasei* TCI058 of the present invention or the metabolite thereof can effectively promote the body weight loss and prevent re-fat of subjects and can be used for the preparation of a composition for reducing body fat.

Example 1

Effect of the *Lactobacillus paracasei* subsp *paracasei* TCI058 on Converting the Fatty Acid into Conjugated Linoleic Acid In the embodiment of the present invention, in order to test the effect of the *Lactobacillus paracasei* subsp *paracasei* TCI058 on converting the fatty acid into conjugated linoleic acid, the fresh milk rich in fatty acids was used to perform the converting test in a test tube in vitro. First, the frozen storage of the *Lactobacillus paracasei* subsp *paracasei* TCI058 of the present invention was activated by MRS culture medium once. After being activated, one percent of the bacteria were transferred into fresh milk, preferably 0.5 mL of the activated bacteria in 50 mL of fresh milk (the concentration of the *Lactobacillus paracasei* subsp *paracasei* TCI058 of the present invention was equivalent to $1 \times 10^6$ cfu/mL). After culturing at 37° C. for 16 hours, the fresh milk (control group) and the milk fermented by the *Lactobacillus paracasei* subsp *paracasei* TCI058 of the present invention were sent to Société Générale de Surveillance, Taiwan for performing the test of General fatty Acid composition.

Conjugated linoleic acids (CLA, known as 9-cis,11-trans-octadecadienoic acid) are the isomer of linoleic acids (LA, known as 10-trans,12-cis-octadecadienoic acid), and like linoleic acid, is an omega-6 unsaturated fatty acid. Conjugated linoleic acid can reduce the accumulation and retention of body fat and promote the conversion of stored fats into energy. Conjugated linoleic acid is mainly derived from ruminant meat, such as mutton, beef, etc. In addition to animal products, safflower seed oil is the source of the highest conjugated linoleic acid in all vegetable oils, and conjugated linoleic acid can be ingested through natural foods; however, the content in food is not high.

The results of the effect of the *Lactobacillus paracasei* subsp *paracasei* TCI058 on converting the fatty acid into conjugated linoleic acid were shown in Table 2. As showing in Table.1, the fresh milk fermented by the *Lactobacillus paracasei* TCI058 of the present invention contains 0.39% of conjugated linoleic acid, and the untreated fresh milk does not contain any conjugated linoleic acids, and the preliminary test results presumably indicates that the *Lactobacillus paracasei* TCI058 of the present invention can effectively convert the fatty acid into conjugated linoleic acid.

TABLE 2

Analysis of conjugated linoleic acids and linoleic acids in fresh milk

| | Fresh milk + TCI 058 | Fresh milk |
|---|---|---|
| 9-cis, 11-trans-octadecadienoic acid (Conjugated linoleic acids) | 0.39% | Not detected |
| 10-trans,12-cis-octadecadienoic acid (Linoleic acids) | Not detected | Not detected |

Example 2

Effect of the *Lactobacillus paracasei* subsp *paracasei* TCI058 on Inhibiting the Accumulation of Fat In the embodiment of the present invention, the effect of the *Lactobacillus paracasei* subsp *paracasei* TCI058 of the present invention on inhibiting the accumulation of fat was tested in mouse bone marrow stromal cells, i.e. OP9 cells. The mouse bone marrow stromal cell line was purchased from the American Type Culture Collection (ATCC) and the number is CRL-2749TM. The cells were cultured in Pre-adipocyte Expansion Medium before differentiation, which contained 90%, of Minimum Essential Medium Alpha Medium (MEMAM) cell culture medium (purchased from Gibco, USA, 12100-046), 10% fetal bovine serum (purchased from Gibco, USA), and 0.1% penicillin/streptomycin (purchased from Gibco, USA). The cells were differentiated by the differentiation medium containing 90% of MESAM cell culture medium, 20% fetal bovine serum, and 0.1% penicillin/streptomycin. The lipids in the cells was stained by the oil red O staining reagent (purchased from Sigma, USA); wherein, 3 mg/mL oil red O stock solution was disposed with 00% isopropanol, and the stock solution was configured to be 60% by $ddH_2O$ as the working solution.

In order to confirm the effect of the *Lactobacillus paracasei* subsp *paracasei* TCI058 on inhibiting the accumulation of fat, firstly, mouse bone marrow stromal cells were differentiated into adipocytes. $8 \times 10^4$ mouse bone marrow stromal cells were cultured in 500 μL of the above-mentioned Pre-adipocyte Expansion Medium in a 24-well plate at 37° C. for 7 days, and then the above-mentioned differentiation medium was changed every 3 days. After 7 days, the formation of lipid droplets was observed under a microscope to ensure that the cells were completely differentiated, and then the fat cells were divided into the following 3 groups: (1) the control group only containing the cell culture medium, (2) the control group only added 0.25% (v/v) of the above-mentioned bacterial culture medium (i.e. empty culture medium), and (3) the experimental group added 0.25% (v/v) of the *Lactobacillus paracasei* subsp *paracasei* TCI058 of the present invention. Each group of cells was cultured at 37° C. for 7-10 days, and the fresh differentiation medium was also replaced every 3 days; wherein, the added material in group (3) was the culture supernatant gotten from culturing 1% of the *Lactobacillus paracasei* subsp *paracasei* TC058 of the present invention in the bacterial culture medium with the concentration of $5 \times 10^8$ cfu/mL at 37° C. for 16 hours.

Then, the intracellular lipids were stained with oil red O to evaluate whether the *Lactobacillus paracasei* subsp *paracasei* TCI058 of the present invention could reduce accumulation of fat. First, the culture medium of each group was gently removed without affecting the cells attached to the bottom of the plate, and the cells were washed twice with 1 mL of phosphate buffered saline (PBS). 1 mL of 10% formaldehyde (purchased from Echo Chemical, Taiwan, Cat. TG1794-4-0000-72NI) was added and reacted at room temperature for 30 minutes to fix the cells, and then the formaldehyde was removed from cells and the cells were gently washed twice with 1 mL of PBS. Then, 1 mL of 60% isopropanol (purchased from Echo Chemical, Taiwan, PH-3101) was added to each well for 1 minute reaction, and then isopropanol was removed and 1 mL of oil red O working solution was added for 1 hour reaction at room temperature. The oil red O working solution was removed and the cells were rapidly decolorized with 1 mL of 60% isopropanol for 5 seconds. Next, 100% isopropanol was added to the stained cells, and cells were placed on a shaker for 10 minutes to dissolve oil droplets, and then 100 μL of the solution from each group was transferred into a 96-well plate. The $OD_{510\ nm}$ readings of each well were gotten by a measurement ELISA reader (BioTek) to quantify the amount of oil red O in each group of cells. The statistically significant difference between each group was determined by the unpaired student's t-test of Excel software (*$p<0.05$;  $p<0.01$; * $p<0.001$).

Figure 2:
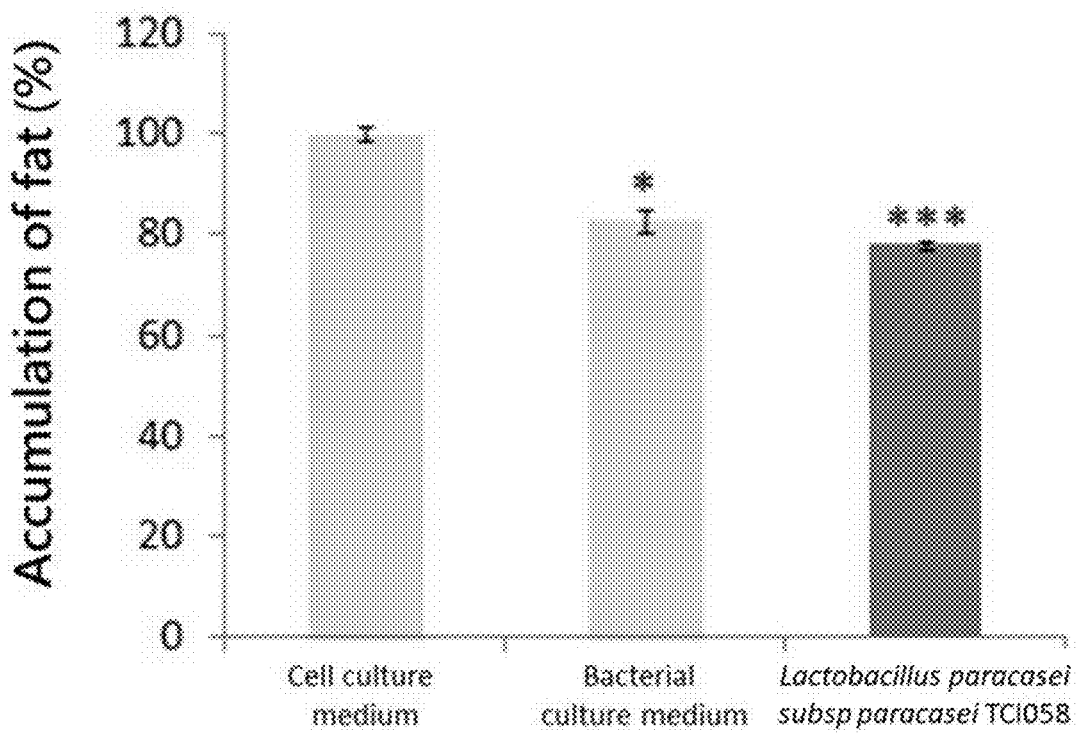
FIG. 2 shows a bar graph that the *Lactobacillus paracasei* subsp *paracasei* TCI058 of the present invention inhibits the accumulation of fat. * $p<0.05$; *** $p<0.001$.

The results of effect of the *Lactobacillus paracasei* subsp *paracasei* TCI058 of the present invention on inhibiting the accumulation of fat were shown in FIG. 2. As showing in FIG. 2, wherein, the read of the control group only containing the cell culture medium was as 100%, after treated with *Lactobacillus paracasei* subsp *paracasei* TCI058 of the present invention, the fat content in the fat cells was significantly reduced with 22% as compared with the control group only containing the cell culture medium. The result indicates that the *Lactobacillus paracasei* subsp *paracasei* TCI058 of the present invention can effectively inhibit the accumulation of fat and reduce the amount of fat in cells.

Example 3

Effect of the *Lactobacillus paracasei* subsp *Paracasei* TCI058 on Promoting the Decomposition of Fat In the embodiment of the present invention, the above-mentioned mouse bone marrow stromal cells were subjected to the test of the effect of the *Lactobacillus paracasei* subsp *paracasei* TCI058 of the present invention on promoting the decomposition of fat. First, the mouse bone marrow stromal cells were differentiated into adipocytes by the experimental procedure in the EXAMPLE 2. Similarly, after 7 days from the start of culture, the formation of lipid droplets was observed under a microscope to ensure that the cells were completely differentiated, and then the fat cells were divided into the following 3 groups: (1) the control group only containing the cell culture medium, (2) the control group only added 0.25% (v/v) of the above-mentioned bacterial culture medium (i.e. empty culture medium), and (3) the experimental group added 0.25% (v/v) of the *Lactobacillus paracasei* subsp *paracasei* TCI058 of the present invention. Similarly, each group of cells was cultured at 37° C. for 7-10 days, and the fresh differentiation medium was also replaced every 3 days; wherein, the added material in group (3) was the culture supernatant gotten from culturing 1% of the *Lactobacillus paracasei* subsp *paracasei* TCI058 of the present invention in the bacterial culture medium with the concentration of $5 \times 10^8$ cfu/mL at 37° C. for 16 hours.

Next, the value of extracellular glycerol was measured by the glycerol detection kit (purchased from Cayman Chemical, USA). If the triglyceride stored in the cells is decomposed free glycerol and fatty acids would be produced; therefore, by measuring the extracellular glycerol content, the value of the decomposition of fat in cells can be inferred. The kit quantifies the extracellular glycerol content by measuring the product content from the coupled enzyme reaction system that produces a bright purple product, and uses the standard to establish a standard curve to derive the extracellular glycerol content of samples. First, the supernatant of cell culture medium from each group was collected and then 25 μL of each collection was transferred into a new 96-well plate, and 100 μL of the reconstituted free glycerol assay reagent was added into each well for 15 minutes reaction at room temperature. Next, the $OD_{540\ nm}$ readings of each well were gotten by a measurement ELISA reader (BioTek). The statistically significant difference between each group was determined by the unpaired student's t-test of Excel software (*$p<0.05$;  $p<0.01$; * $p<0.001$).

Figure 3:
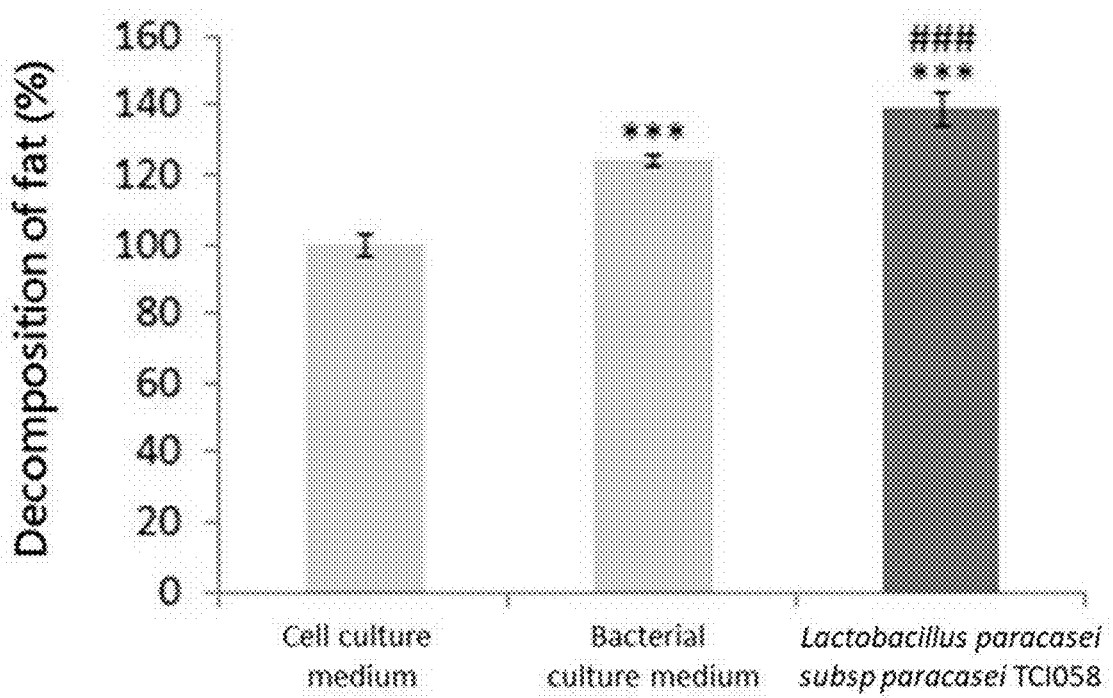
FIG. 3 shows a bar graph that the *Lactobacillus paracasei* subsp *paracasei* TCI058 of the present invention promotes the decomposition of fat. Compared with the control group only containing the cell culture medium: *** $p<0.001$; compared with the control group containing bacterial culture medium: ### $p<0.001$.

The results of effect of the *Lactobacillus paracasei* subsp *paracasei* TCI058 of the present invention on promoting the decomposition of fat were shown in FIG. 3. As showing in FIG. 3, wherein, the read of the control group only containing the cell culture medium was as 100%, after treated with *Lactobacillus paracasei* subsp *paracasei* TCI058 of the present invention, the decomposition of fat in the fat cells was significantly increased with 39% as compared with the control group only containing the cell culture medium. The result indicates that the *Lactobacillus paracasei* subsp *paracasei* TCI058 of the present invention can effectively promote the decomposition of fat and reduce the amount of fat in cells.

Example 4

Effect of the *Lactobacillus paracasei* subsp *paracasei* TCI058 on Promoting Weight Loss of Individuals In the embodiment of the present invention, in order to test the effect of the *Lactobacillus paracasei* subsp *paracasei* TCI058 of the present invention on promoting weight loss of individuals. 7 male or female aged 25-55 subjects were recruited; wherein, the BMI of the subjects was higher than or equal to 24 and the body fat of the male subjects was higher than 25% and the female subjects was higher than 30%. The subjects took capsule containing $5\times10^9$ cfu the *Lactobacillus paracasei* subsp *paracasei* TCI058 of the present invention after daily lunch. Next, the determination of body weight indicators of each subject, including the body weight, the waist circumference, the percentage of body fat and the muscle mass, was measured before and after two weeks of the treatment. Besides, the defecation questionnaire was filled in by each subject, and the defecation questionnaire was shown as Table 3.

TABLE 3

| The defecation questionnaire |
|---|
| 1. How long does it take to defecate in a week before/after the treatment?<br>❏ More than twice a day ❏ Once a day ❏ Once every two days<br>❏ Once every three days ❏ Once every four days ❏ others |
| 2. Immediate gastrointestinal sensation of defecate before/after the treatment?<br>❏ Super feeling ❏ Ordinary feeling ❏ Few feeling ❏ No feeling |
| 3. What time does it take to defecate before/after the treatment?<br>❏ Less than 5 minutes ❏ 5-10 minutes ❏ 10-20 minutes |
| 4. How laborious is it during defecation before/after the treatment?<br>❏ No effort, easy and smooth ❏ Need some effort<br>❏ Need lots of effort |

Figure 4:
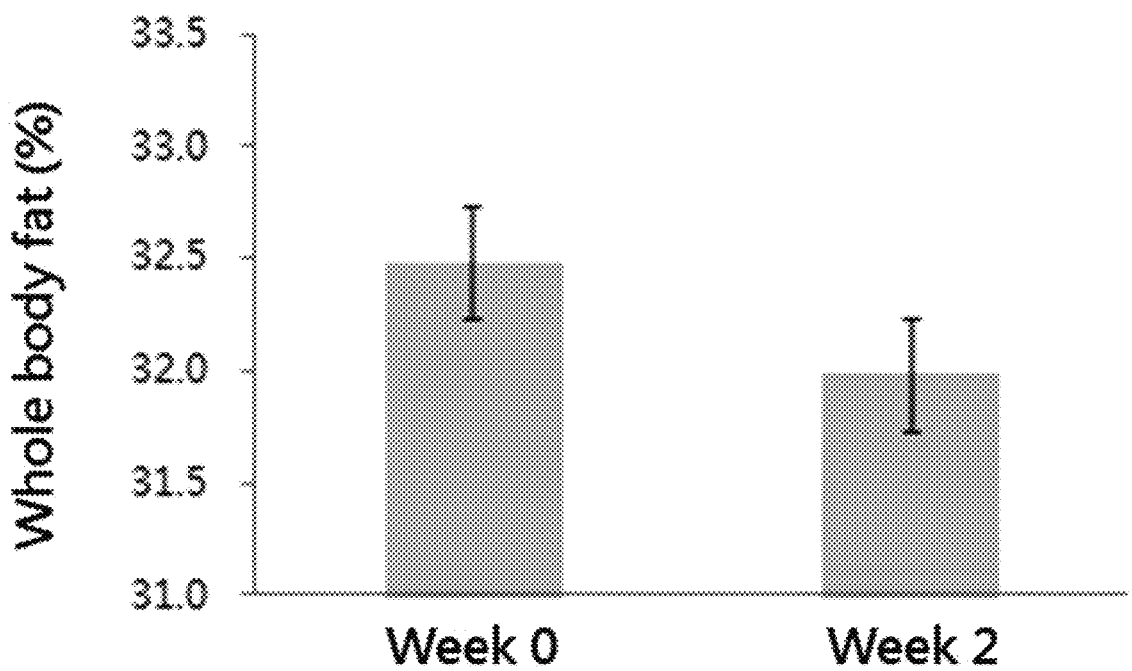
FIG. 4 shows a bar graph that the *Lactobacillus paracasei* subsp *paracasei* TCI058 of the present invention reduces the percentage of whole body fat.

The results of effect of the *Lactobacillus paracasei* subsp *paracasei* TCI058 of the present invention on reducing the percentage of whole body fat were shown in FIG. 4. As showing in FIG. 4, the mean percentage of whole body fat of the subject before the treatment was about 32.5%; after taking the *Lactobacillus paracasei* subsp *paracasei* TC058 for two weeks, the mean percentage of whole body fat of the subject can be reduced to 32%, and the whole body fat can be reduced by 0.5%.

Figure 5:
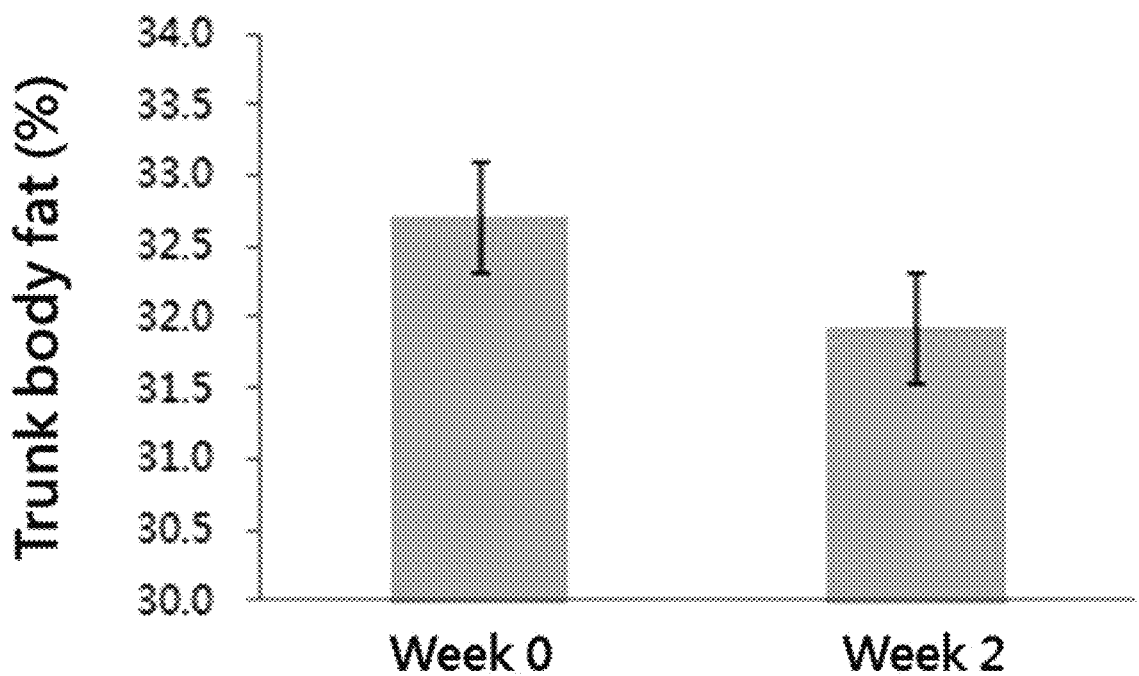
FIG. 5 shows a bar graph that the *Lactobacillus paracasei* subsp *paracasei* TCI058 of the present invention reduces the percentage of trunk body fat.

The results of effect of the *Lactobacillus paracasei* subsp *paracasei* TCI058 of the present invention on reducing the percentage of trunk body fat were shown in FIG. 5. As showing in FIG. 5, the mean percentage of trunk body fat of the subject before the treatment was about 32.7%; after taking the *Lactobacillus paracasei* subsp *paracasei* TCI058 for two weeks, the mean percentage of trunk body fat of the subject can be reduced to 31.9%, and the trunk body fat can be reduced by 0.8%.

Figure 6:
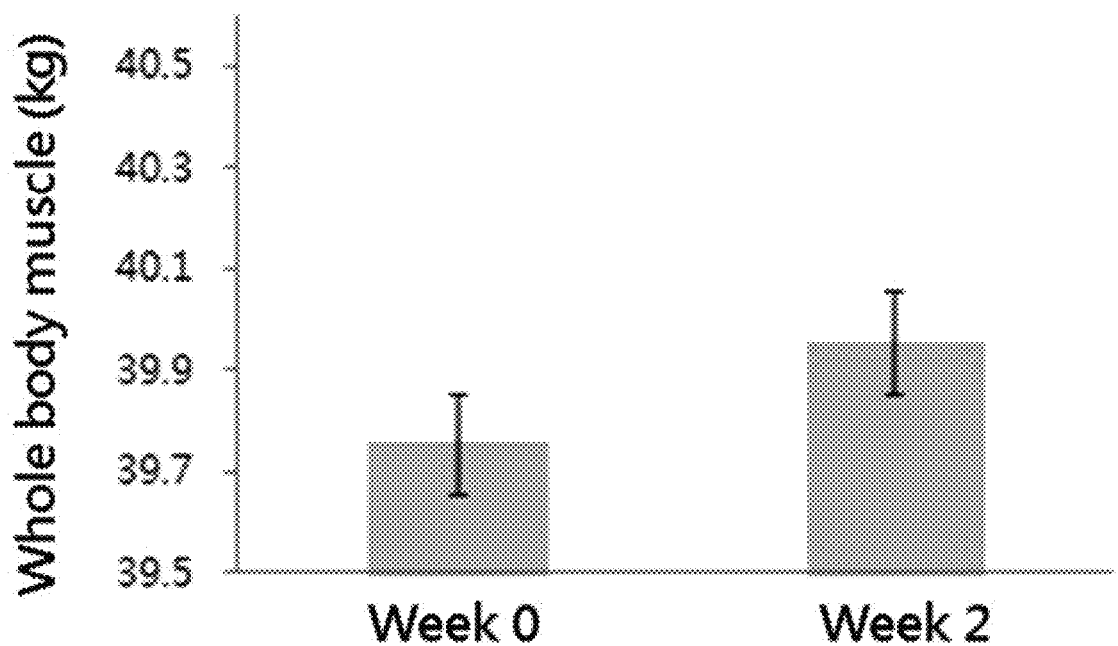
FIG. 6 shows a bar graph that the *Lactobacillus paracasei* subsp *paracasei* TCI058 of the present invention increases the whole body muscle.

The results of effect of the *Lactobacillus paracasei* subsp *paracasei* TCI058 of the present invention on increasing the whole body muscle were shown in FIG. 6. As showing in FIG. 6, the mean whole body muscle of the subject before the treatment was about 39.8 kg; after taking the *Lactobacillus paracasei* subsp *paracasei* TCI058 for two weeks, the mean whole body muscle of the subject can be increased to 40 kg, and the whole body muscle can be increased by 0.2 kg.

Figure 7:
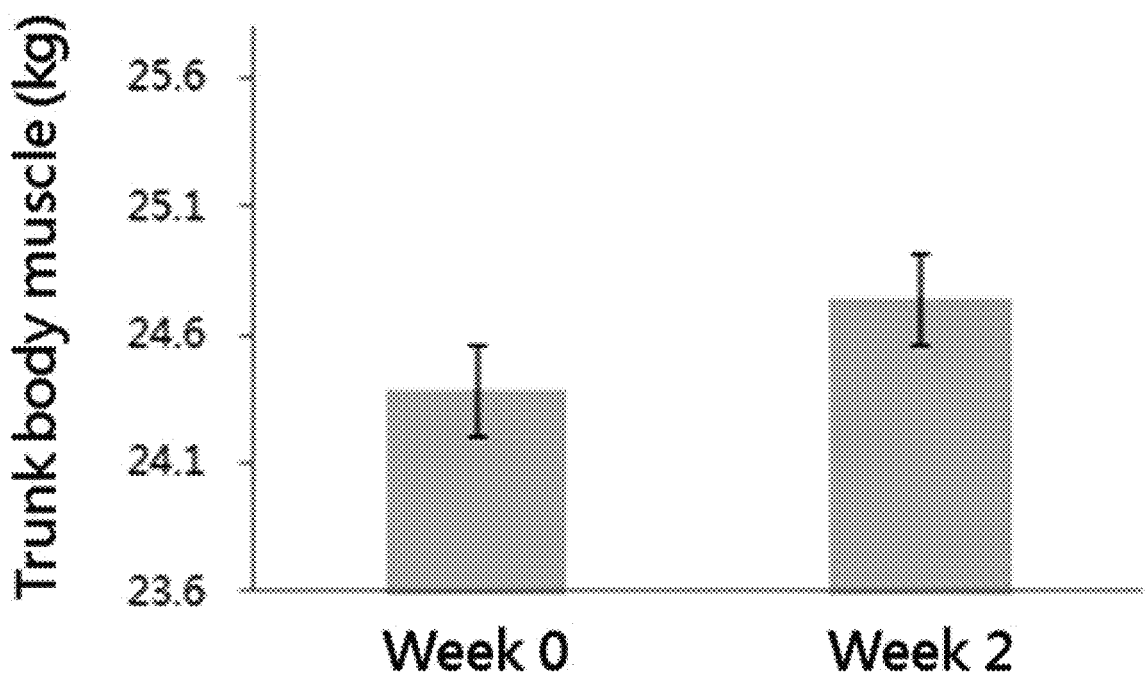
FIG. 7 shows a bar graph that the *Lactobacillus paracasei* subsp *paracasei* TCI058 of the present invention increases the trunk muscle.

The results of effect of the *Lactobacillus paracasei* subsp *paracasei* TCI058 of the present invention on increasing the trunk muscle were shown in FIG. 7. As showing in FIG. 7, the mean trunk muscle of the subject before the treatment was about 24.4 kg; after taking the *Lactobacillus paracasei* subsp *paracasei* TCI058 for two weeks, the mean trunk muscle of the subject can be increased to 24.8 kg, and the trunk muscle can be increased by 0.4 kg.

Figure 8:
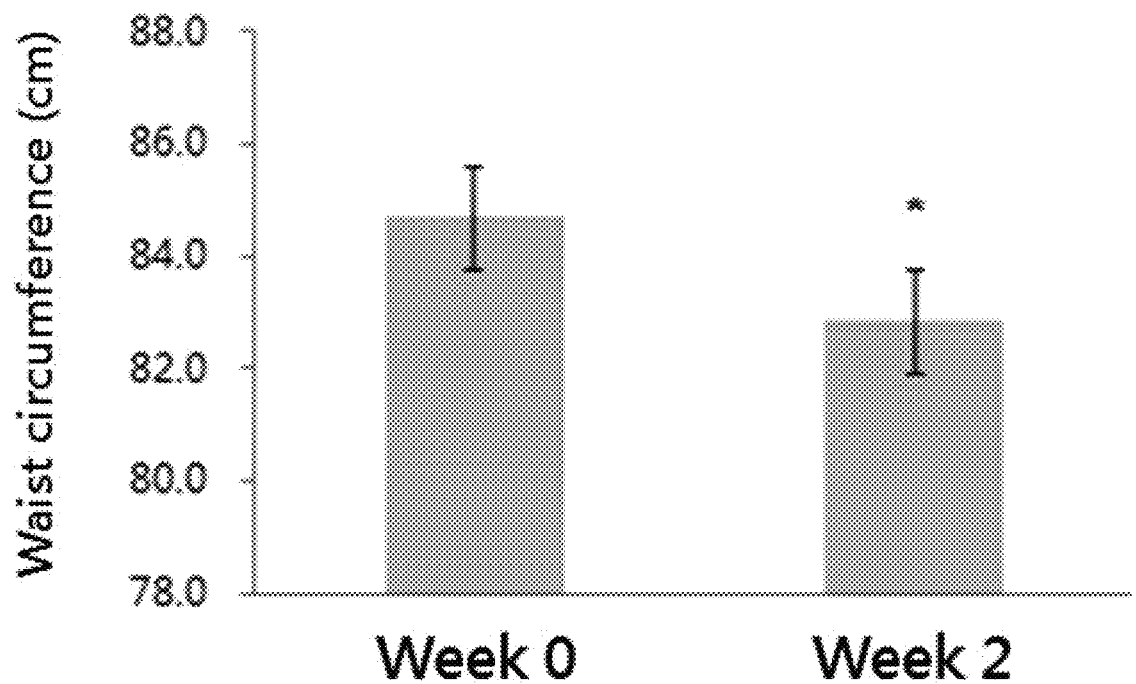
FIG. 8 shows a bar graph that the *Lactobacillus paracasei* subsp *paracasei* TCI058 of the present invention reduces the waist circumference. * $p<0.05$.

The results of effect of the *Lactobacillus paracasei* subsp *paracasei* TCI058 of the present invention on reducing the waist circumference were shown in FIG. 8. As showing in FIG. 8, the mean waist circumference of the subject before the treatment was about 85 cm; after taking the *Lactobacillus paracasei* subsp *paracasei* TCI058 for two weeks, the mean waist circumference of the subject can be reduced to 83.2 cm, and the waist circumference can be reduced by 1.8 cm.

Figure 9:
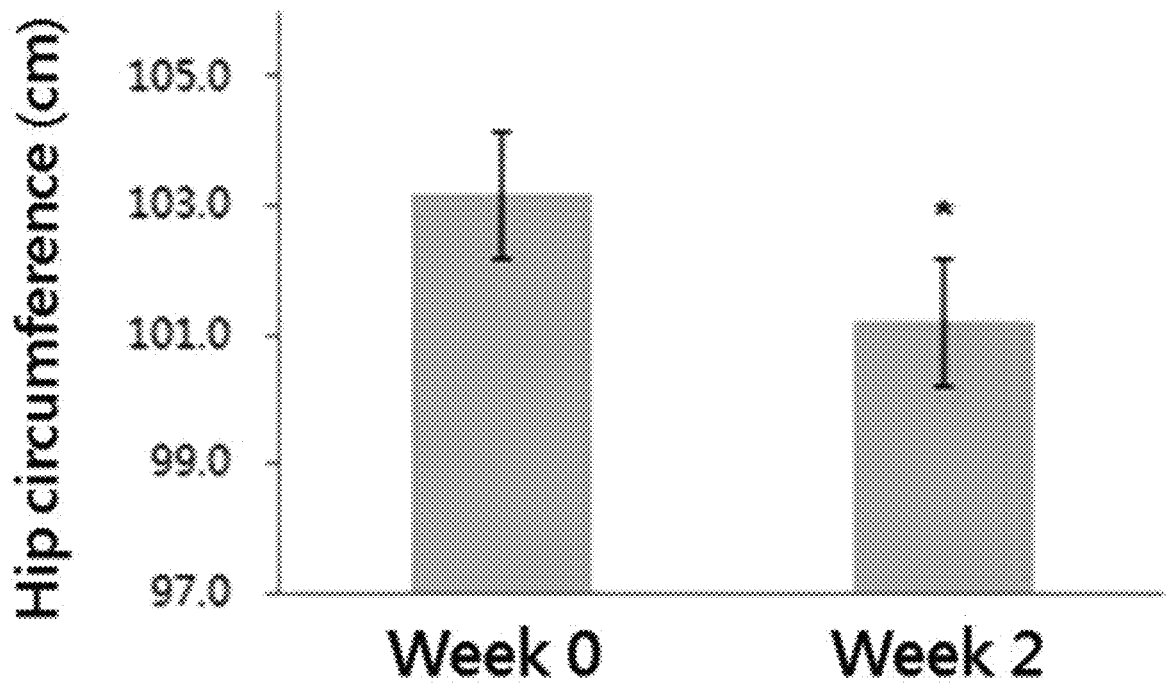
FIG. 9 shows a bar graph that the *Lactobacillus paracasei* subsp *paracasei* TCI058 of the present invention reduces the hip circumference. * $p<0.05$.

The results of effect of the *Lactobacillus paracasei* subsp *paracasei* TCI058 of the present invention on reducing the hip circumference were shown in FIG. 9. As showing in FIG. 9, the mean hip circumference of the subject before the treatment was about 103 cm; after taking the *Lactobacillus paracasei* subsp *paracasei* TCI058 for two weeks, the mean hip circumference of the subject can be reduced to 101 cm, and the hip circumference can be reduced by 2 cm.

The results indicate that the *Lactobacillus paracasei* subsp *paracasei* TCI058 of the present invention can effectively reduce the percentage of whole body fat, the percentage of trunk body fat, the waist circumference, and the hip circumference of the subject, and simultaneously increase the whole body muscle, and the trunk muscle mass and therefore can effectively promote the body weight loss and prevent re-fat of subjects.

In summary, the active strain of the *Lactobacillus paracasei* subsp *paracasei* TCI058 or the metabolite thereof can effectively convert the fatty acid in food into conjugated linoleic acid in vitro, which indicates that the *Lactobacillus paracasei* subsp *paracasei* TCI058 or the metabolite thereof has the potential to reduce the accumulation and retention of body fat in a subject and to promote the conversion of stored fat in a subject into energy. In the cell experiment, the *Lactobacillus paracasei* subsp *paracasei* TCI058 of the present invention or the metabolite thereof was found can effectively inhibit the accumulation of fat in fat cells and at the same time effectively promote the decomposition of fat in fat cells to reduce the content of fat in fat cells. In body experiments, the *Lactobacillus paracasei* subsp *paracasei* TCI058 of the present invention or the metabolite thereof was found can effectively reduce the percentage of whole body fat, the percentage of trunk body fat, the waist circumference, and the hip circumference of the subject, and can simultaneously increase the whole body muscle, or the trunk muscle mass to effectively reduce the fat content in subjects, and promote the body weight loss and prevent re-fat of subjects. Therefore, the *Lactobacillus paracasei* subsp *paracasei* TCI058 of the present invention or the metabolite thereof can be used for the preparation of a composition for reducing body fat, which is a food, a drink, a nutritional supplement, or a pharmaceutical product, and the composition is in a form of a powder, a granule, a solution, a gel can be administered to a subject in need by oral administration or the like.

What is claimed is:

1. A method of reducing body fat, comprising administering a composition comprising $5\times10^9$ CPUs per day of *Lactobacillus paracasei* subsp *paracasei* DSMZ33286 or the metabolite thereof to a subject in need thereof.

2. The method according to claim 1, wherein the *Lactobacillus paracasei* subsp *paracasei* DSMZ33286 or the metabolite thereof converts a fatty acid to a conjugated linoleic acid.

3. The method according to claim 2, wherein the effective amount of the *Lactobacillus paracasei* subsp *paracasei* DSMZ33286 is $1\times10^6$ CPUs per day.

4. The method according to claim 1, wherein the *Lactobacillus paracasei* subsp *paracasei* DSMZ33286 or the metabolite thereof inhibits the accumulation of fat in a fat cell or promotes the breakdown of fat in a fat cell.

5. The method according to claim 1, wherein the *Lactobacillus paracasei* subsp *paracasei* DSMZ33286 or the metabolite thereof reduces the percentage of whole body fat, the percentage of trunk body fat, the waist circumference, or the hip circumference of the subject.

6. The method according to claim 1, wherein the *Lactobacillus paracasei* subsp *paracasei* DSMZ33286 or the metabolite thereof increases the whole body muscle, or the trunk muscle mass.

7. The composition according to claim 1, wherein the composition is in the form of a powder, a granule, a solution, or a gel.

8. The composition according to claim 6, wherein the composition is selected from the group consisting of a food, a drink, a nutritional supplement, and a pharmaceutical product.

\* \* \* \* \*